United States Patent
Kim et al.

(10) Patent No.: US 11,377,516 B2
(45) Date of Patent: Jul. 5, 2022

(54) LOW EMISSION POLYOXYMETHYLENE COMPOSITION

(71) Applicant: Ticona LLC, Florence, KY (US)

(72) Inventors: Sung Hye Kim, Erlanger, KY (US); Rong Luo, Florence, KY (US); Jared T. Kindt, Union, KY (US)

(73) Assignee: Ticona LLC, Florence, KY (US)

( * ) Notice: Subject to any disclaimer, the term of this patent is extended or adjusted under 35 U.S.C. 154(b) by 0 days.

(21) Appl. No.: 16/869,304

(22) Filed: May 7, 2020

(65) Prior Publication Data

US 2020/0262962 A1 Aug. 20, 2020

Related U.S. Application Data

(62) Division of application No. 15/947,228, filed on Apr. 6, 2018, now Pat. No. 10,676,558.

(60) Provisional application No. 62/483,108, filed on Apr. 7, 2017.

(51) Int. Cl.
| | |
|---|---|
| C08K 5/3445 | (2006.01) |
| C08K 5/3492 | (2006.01) |
| C08L 59/04 | (2006.01) |
| C08G 2/08 | (2006.01) |
| C08K 5/17 | (2006.01) |
| C08L 61/02 | (2006.01) |
| C08K 5/00 | (2006.01) |
| C08L 59/02 | (2006.01) |
| C08K 5/16 | (2006.01) |
| C08K 5/31 | (2006.01) |
| A61M 15/00 | (2006.01) |
| A61M 5/31 | (2006.01) |
| A61M 5/178 | (2006.01) |

(52) U.S. Cl.
CPC .............. *C08G 2/08* (2013.01); *C08K 5/005* (2013.01); *C08K 5/0083* (2013.01); *C08K 5/16* (2013.01); *C08K 5/175* (2013.01); *C08K 5/31* (2013.01); *C08K 5/3445* (2013.01); *C08K 5/3492* (2013.01); *C08L 59/02* (2013.01); *C08L 59/04* (2013.01); *C08L 61/02* (2013.01); *A61M 5/178* (2013.01); *A61M 5/31* (2013.01); *A61M 15/00* (2013.01); *A61M 15/0001* (2014.02); *A61M 2205/02* (2013.01); *A61M 2207/10* (2013.01); *C08L 2203/02* (2013.01)

(58) Field of Classification Search
CPC ...................................................... C08G 2/08
USPC ........................................................ 528/243
See application file for complete search history.

(56) References Cited

U.S. PATENT DOCUMENTS

| | | | |
|---|---|---|---|
| 7,638,565 B2 | 12/2009 | Harashina | |
| 10,676,558 B2* | 6/2020 | Kim | C08K 5/31 |
| 2004/0010064 A1 | 1/2004 | Harashina et al. | |
| 2006/0052492 A1* | 3/2006 | Harashina | C08K 5/3492 |
| | | | 524/100 |
| 2007/0073007 A1 | 3/2007 | Harashina | |
| 2009/0143506 A1* | 6/2009 | Harashina | B01J 20/22 |
| | | | 524/91 |
| 2011/0034610 A1* | 2/2011 | Mulholland | C08K 3/08 |
| 2014/0179840 A1* | 6/2014 | Tyler | C08K 5/3475 |
| | | | 524/94 |
| 2018/0258278 A1* | 9/2018 | Zia | B66C 23/701 |

OTHER PUBLICATIONS

Supplementary European Search Report and Annex to the European Search Report Corresponding to Application No. EP 18780886 dated Jan. 13, 2021.

Chinese Office Action & Search Report Corresponding to Application No. 201880033527 dated Mar. 31, 2022.

\* cited by examiner

*Primary Examiner* — Marc S Zimmer
(74) *Attorney, Agent, or Firm* — Dority & Manning, P.A.

(57) ABSTRACT

A polyoxymethylene polymer composition is disclosed containing a formaldehyde stabilizer package. The formaldehyde stabilizer package, which contains at least two emission control agents, dramatically and unexpectedly reduces formaldehyde emissions. The formaldehyde stabilizer package includes at least two emission control agents selected from the group of benzoguanamine compounds, a hydantoin, a substituted hydantoin, an amino acid, and an alkylene urea such as ethylene urea.

15 Claims, 3 Drawing Sheets

LOW EMISSION POLYOXYMETHYLENE COMPOSITION

RELATED APPLICATIONS

The present application is a divisional application of U.S. patent application Ser. No. 15/947,228, having a filing date of Apr. 6, 2018, which is based on and claims priority to U.S. Provisional Patent Application Ser. No. 62/483,108, having a filing date of Apr. 7, 2017, both of which are incorporated herein by reference.

BACKGROUND

Polyacetal polymers, which are commonly referred to as polyoxymethylenes, have become established as exceptionally useful engineering materials in a variety of applications. Polyoxymethylene polymers, for instance, are widely used in constructing molded parts, such as parts for use in the automotive industry and the electrical industry. Polyoxymethylene polymers, for instance, have excellent mechanical properties, fatigue resistance, abrasion resistance, chemical resistance, and moldability.

Although polyacetal resins possess many useful properties, the polymers have a tendency to degrade when heated and are inherently unstable in an oxidative atmosphere or in an acidic or alkaline environment. In particular, polyacetal resins have a tendency to emit formaldehyde during processing and after the polymer has been molded into a part. Formaldehyde is not only a contaminant, but can also adversely affect metallic components that may be placed in association with the polymer. For example, formaldehyde readily oxidizes to formic acid which can corrode metals or cause discoloration.

In view of the above, those skilled in the art have attempted to combine polyacetal polymers with various compounds in order to lower formaldehyde emissions. For instance, in the past, polyacetal polymers have been combined with melamines in order to achieve lower formaldehyde emission performance. In addition, various other chemical compounds have been suggested for lowering formaldehyde emissions.

Although various chemical compounds used in the past have successfully lowered formaldehyde emissions from products made from polyoxymethylene polymers, further improvements in formaldehyde emissions are needed. For instance, stricter government regulations continue to require further improvements in reducing formaldehyde emissions.

Unfortunately, however, when additives are combined with a polyacetal polymer in order to enhance one property, the additive may have an adverse impact on another property. For example, adding greater amounts of formaldehyde scavengers into polyoxymethylene polymer compositions can compromise one or more properties of the polymer. For instance, excess amounts of formaldehyde scavengers may increase the occurrence of mold deposits and/or begin to adversely affect other physical properties.

In view of the above, a need exists for an improved formaldehyde stabilizer package capable of further reducing formaldehyde emissions without adversely affecting other properties of the polyoxymethylene polymer composition.

SUMMARY

In general, the present disclosure is directed to a polymer composition containing primarily a polyacetal resin and to molded products made from the composition. The polymer composition of the present disclosure is particularly formulated to exhibit ultra-low formaldehyde emissions. For example, polyoxymethylene polymer compositions formulated in accordance with the present disclosure can exhibit a formaldehyde emission when tested according to VDA Test 275 of less than about 5 ppm, such as less than about 4 ppm, such as even less than about 3 ppm. The VDA 275 Test (German Automotive Industry Recommendation No. 275) is documented by Kraftfahrwesen e. V., July 1994.

In one embodiment, for instance, the polymer composition of the present disclosure comprises a polyoxymethylene polymer in combination with a formaldehyde stabilizer package for reducing formaldehyde emissions. The formaldehyde stabilizer package, in one embodiment, can comprise a blend of emission control agents. The blend includes at least two emission control agents selected from a guanamine compound, a hydantoin, a substituted hydantoin, an amino acid, and an alkylene urea such as an ethylene urea. For instance, in one embodiment, the formaldehyde stabilizer package may comprise a blend of a guanamine compound and a substituted hydantoin, such as allantoin. Alternatively, the formaldehyde stabilizer package may comprise a blend of a guanamine compound and a hydantoin. In still another embodiment, the formaldehyde stabilizer package comprises a blend of a guanamine compound and an amino acid. The amino acid, for instance, may comprise arginine. The substituted hydantoin, the hydantoin, or the amino acid may be present in the polymer composition generally in an amount less than about 0.5% by weight, such as in an amount less than about 0.3% by weight, such as in an amount less than about 0.2% by weight. The above emission control agents are generally present in the polymer composition in an amount greater than about 0.001% by weight.

In one embodiment, the guanamine compound comprises benzoguanamine. When present, the benzoguanamine can be included in the composition in an amount greater than about 0.2% by weight, such as in an amount greater than about 0.3% by weight, such as in an amount greater than about 0.4% by weight and generally in an amount less than about 2% by weight, such as in an amount less than about 1.5% by weight. The guanamine compound can be present in relation to another emission control agent at a weight ratio of from about 20:1 to about 1:1, such as from about 15:1 to about 2:1, such as from about 8:1 to about 3:1.

In an alternative embodiment, especially when the polyoxymethylene polymer composition is used for producing medical products, the formaldehyde stabilizer package comprises a blend of a substituted hydantoin and an amino acid. The substituted hydantoin may comprise allantoin. The amino acid may comprise arginine.

In one embodiment, the formaldehyde stabilizer package contains an ethylene urea, such as in an amount from about 0.001% by weight to about 5% by weight. The ethylene urea can be combined with any of the other formaldehyde stabilizers described above including benzoguanimine and/or allantoin.

In general, any suitable polyoxymethylene polymer may be contained in the polymer composition. In one embodiment, the polyoxymethylene polymer has a melt flow rate of from about 5 $cm^3$/10 min to about 15 $cm^3$/10 min. In an alternative embodiment, the polyoxymethylene polymer has a melt flow rate of from about 18 $cm^3$/10 min to about 40 $cm^3$/10 min.

Various other additives may be contained in the polymer composition. In one embodiment, for instance, the composition further contains an acid scavenger, such as a calcium salt. The composition can also contain a coloring agent. The coloring agent can be present in the composition in an amount from about 0.1% by weight to about 5% by weight. When a coloring agent is present in the composition, the acid scavenger may comprise calcium propionate.

In one embodiment, the polymer composition contains a nucleant in an amount from about 0.05% by weight to about 1% by weight, an antioxidant in an amount from about 0.05% to about 2% by weight, and a lubricant in an amount from about 0.05% to about 1.5% by weight.

In one embodiment, the polymer composition may include an impact modifier. The impact modifier, for instance, may comprise a thermoplastic elastomer, such as a thermoplastic polyurethane elastomer. The impact modifier can be present in an amount from about 5% by weight to about 30% by weight.

The polymer composition can also contain one or more reinforcing agents. The reinforcing agent, for instance, may comprise reinforcing fibers, such as glass fibers. Reinforcing fibers can be present in the polymer composition generally in an amount from about 3% by weight to about 40% by weight.

In one embodiment, the polymer composition can also include a UV stabilizer.

Polymer compositions made in accordance with the present disclosure can have an excellent balance of physical properties. For instance, the polymer composition can have a tensile modulus of at least 1200 MPa when tested according to ISO Test 527 at 23° C., can have a tensile strain at yield of greater than about 7% when tested according to ISO Test 527 at 23° C., and can have a notched Charpy impact strength of greater than about 3 kJ/m$^2$ when tested according to ISO Test 179-1 at 23° C.

Various different and diverse articles can be molded from the polymer composition. Due to the low formaldehyde emissions, the polymer composition is particularly well suited to producing molded articles for the interior of an automobile. The molded article may comprise, for instance, a latch, a lever, a gear, a pivot housing, a decorative trim piece, a door handle, a bracket, a speaker grill, or a seat rail. Alternatively, the polymer composition may be used to produce a medical product. The medical product, for instance, may comprise an inhaler or an injector.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
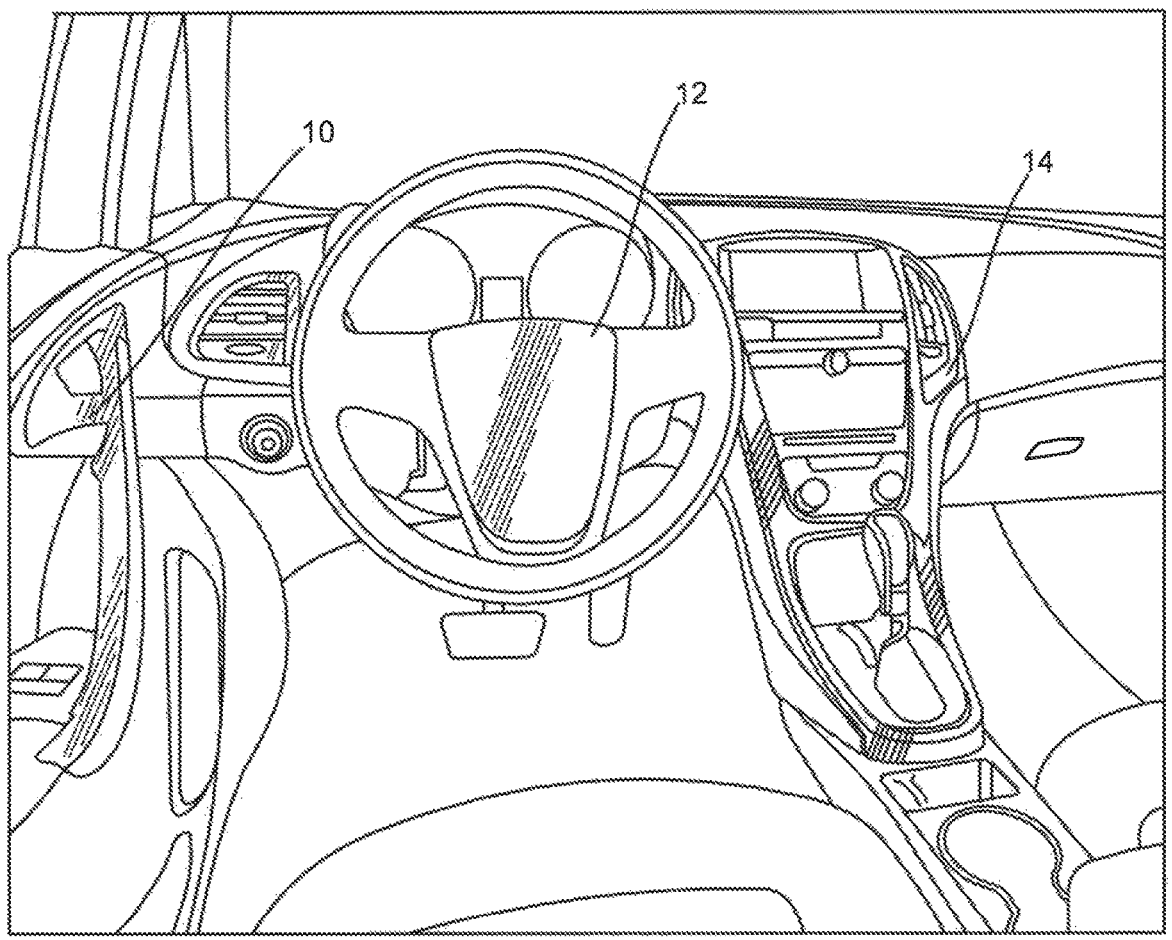
FIG. 1 is a perspective view of the interior of an automobile illustrating various molded articles that may be made in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only and is not intended as limiting the broader aspects of the present disclosure.

In general, the present disclosure is directed to a polymer composition containing a polyacetal resin, particularly a polyoxymethylene copolymer, that exhibits low formaldehyde emissions. The polymer composition is well suited for use in molding processes for producing molded articles. The polymer composition can contain one or more coloring agents for producing molded articles having any desired color. The molded articles can be used in a limitless variety of different applications and in multiple fields. In one embodiment, for instance, molded articles may be made according to the present disclosure that are designed to function as automotive parts, such as automotive parts designed to be used in the interior of vehicles, such as cars and trucks.

More particularly, the present disclosure is directed to a polymer composition containing a polyacetal resin in combination with a formaldehyde stabilizer package. The formaldehyde stabilizer package comprises a blend of emission control agents. Emission control agents that can be used in the formaldehyde stabilizer package include guanamine compounds, a hydantoin, a substituted hydantoin, an amino acid, and an alkylene urea such as an ethylene urea. The guanamine compound, for instance, may comprise a benzoguanamine.

In one embodiment, the formaldehyde stabilizer package comprises a blend of a guanamine compound and at least one of a hydantoin, a substituted hydantoin, an amino acid, or an ethylene urea. In one embodiment, for instance, the formaldehyde stabilizer package comprises a combination of a guanamine compound and allantoin, which is a substituted hydantoin. Alternatively, the formaldehyde stabilizer package may comprise a mixture of a guanamine compound with an amino acid, such as arginine. In some embodiments, the formaldehyde stabilizer package dramatically and efficiently lowers formaldehyde emissions from the polymer composition without compromising other properties.

For instance, in one embodiment, the polymer composition containing the polyoxymethylene polymer exhibits a formaldehyde emission pursuant to VDA 275 of less than about 5 ppm (µg/g), such as less than about 4 ppm, such as less than about 3 ppm. The formaldehyde emission of the polymer composition may be substantially zero.

In general, any suitable polyoxymethylene polymer may be incorporated into the polymer composition.

The preparation of the polyoxymethylene polymer can be carried out by polymerization of polyoxymethylene-forming monomers, such as trioxane or a mixture of trioxane and a cyclic acetal such as dioxolane in the presence of a molecular weight regulator, such as a glycol. The polyoxymethylene polymer used in the polymer composition may comprise a homopolymer or a copolymer. According to one embodiment, the polyoxymethylene is a homo- or copolymer which comprises at least 50 mol. %, such as at least 75 mol. %, such as at least 90 mol. % and such as even at least 97 mol. % of —$CH_2O$-repeat units.

In one embodiment, a polyoxymethylene copolymer is used. The copolymer can contain from about 0.01 mol. % to about 20 mol. % and in particular from about 0.5 mol. % to about 10 mol. % of repeat units that comprise a saturated or ethylenically unsaturated alkylene group having at least 2 carbon atoms, or a cycloalkylene group, which has sulfur atoms or oxygen atoms in the chain and may include one or more substituents selected from the group consisting of alkyl cycloalkyl, aryl, aralkyl, heteroaryl, halogen or alkoxy. In one embodiment, a cyclic ether or acetal is used that can be introduced into the copolymer via a ring-opening reaction.

Preferred cyclic ethers or acetals are those of the formula:

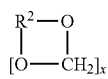

in which x is 0 or 1 and $R^2$ is a $C_2$-$C_4$-alkylene group which, if appropriate, has one or more substituents which are $C_1$-$C_4$-akyl groups, or are $C_1$-$C_4$-alkoxy groups, and/or are halogen atoms, preferably chlorine atoms. Merely by way of example, mention may be made of ethylene oxide, propylene 1,2-oxide, butylene 1,2-oxide, butylene 1,3-oxide, 1,3-dioxane, 1,3-dioxolane, and 1,3-dioxepan as cyclic ethers, and also of linear oligo- or polyformals, such as polydioxolane or polydioxepan, as comonomers. It is particularly advantageous to use copolymers composed of from 99.5 to 95 mol. % of trioxane and of from 0.01 to 5 mol. %, such as from 0.5 to 4 mol. %, of one of the above-mentioned comonomers. In one embodiment, the polyoxymethylene polymer contains relatively low amounts of comonomer. For instance, the comonomer can be present in an amount less than about 2 mol. %, such as less than about 1.5 mol. %, such as less than about 1 mol. %, such as less than about 0.8 mol. %, such as less than about 0.6 mol. %.

The polymerization can be effected as precipitation polymerization or in the melt. By a suitable choice of the polymerization parameters, such as duration of polymerization or amount of molecular weight regulator, the molecular weight and hence the MVR value of the resulting polymer can be adjusted.

In one embodiment, the polyoxymethylene polymer used in the polymer composition may contain a relatively high amount of reactive groups or functional groups in the terminal positions. The reactive groups, for instance, may comprise —OH or —$NH_2$ groups.

In one embodiment, the polyoxymethylene polymer can have terminal hydroxyl groups, for example hydroxyethylene groups and/or hydroxyl side groups, in at least more than about 50% of all the terminal sites on the polymer. For instance, the polyoxymethylene polymer may have at least about 70%, such as at least about 80%, such as at least about 85% of its terminal groups be hydroxyl groups, based on the total number of terminal groups present. It should be understood that the total number of terminal groups present includes all side terminal groups.

In one embodiment, the polyoxymethylene polymer has a content of terminal hydroxyl groups of at least 15 mmol/kg, such as at least 18 mmol/kg, such as at least 20 mmol/kg. In one embodiment, the terminal hydroxyl group content ranges from 18 to 50 mmol/kg. In an alternative embodiment, the polyoxymethylene polymer may contain terminal hydroxyl groups in an amount less than 20 mmol/kg, such as less than 18 mmol/kg, such as less than 15 mmol/kg. For instance, the polyoxymethylene polymer may contain terminal hydroxyl groups in an amount from about 5 mmol/kg to about 20 mmol/kg, such as from about 5 mmol/kg to about 15 mmol/kg. For example, a polyoxymethylene polymer may be used that has a lower terminal hydroxyl group content but has a higher melt volume flow rate.

In addition to or instead of the terminal hydroxyl groups, the polyoxymethylene polymer may also have other terminal groups usual for these polymers. Examples of these are alkoxy groups, formate groups, acetate groups or aldehyde groups. According to one embodiment, the polyoxymethylene is a homo- or copolymer which comprises at least 50 mol-%, such as at least 75 mol-%, such as at least 90 mol-% and such as even at least 95 mol-% of —$CH_2$O-repeat units.

In one embodiment, a polyoxymethylene polymer can be produced using a cationic polymerization process followed by solution hydrolysis to remove any unstable end groups. During cationic polymerization, a glycol, such as ethylene glycol or methylal can be used as a chain terminating agent. A heteropoly acid, triflic acid or a boron compound may be used as the catalyst.

The polyoxymethylene polymer can have any suitable molecular weight. The molecular weight of the polymer, for instance, can be from about 4,000 grams per mole to about 20,000 g/mol. In other embodiments, however, the molecular weight can be well above 20,000 g/mol, such as from about 20,000 g/mol to about 100,000 g/mol.

The polyoxymethylene polymer present in the composition can generally have a melt flow index (MFI) ranging from about 0.1 to about 80 $cm^3$/10 min, as determined according to ISO 1133 at 190° C. and 2.16 kg. In one embodiment, the polyoxymethylene polymer may have a melt flow index of from about 5 $cm^3$/10 min to about 15 $cm^3$/10 min, such as from about 8 $cm^3$/10 min to about 12 $cm^3$/10 min. In an alternative embodiment, a polyoxymethylene polymer may be used that has a relatively high melt flow index. For instance, the polyoxymethylene polymer may have a melt flow index of from about 18 $cm^3$/10 min to about 40 $cm^3$/10 min, such as from about 20 $cm^3$/10 min to about 35 $cm^3$/10 min.

Suitable commercially available polyoxymethylene polymers are available under the trade name Hostaform® (HF) by Celanese.

The polyoxymethylene polymer may be present in the polyoxymethylene polymer composition in an amount of at least 50 wt. %, such as at least 60 wt. %, such as at least 70 wt. %, such as at least 80 wt. %, such as at least 85 wt. %, such as at least 90 wt. %, such as at least 93 wt. %. In general, the polyoxymethylene polymer is present in an amount of less than about 100 wt. %, such as less than about 99 wt. %, such as less than about 97 wt. %, wherein the weight is based on the total weight of the polyoxymethylene polymer composition.

The polyoxymethylene polymer as described above is combined with a formaldehyde stabilizer package that dramatically and efficiently reduces formaldehyde emissions from the polymer composition. The formaldehyde stabilizer package of the present disclosure comprises a blend of emission control agents. For instance, the blend includes at least two emission control agents selected from the group including guanamine compounds, a hydantoin, a substituted hydantoin, an amino acid, and an alkylene urea such as an ethylene urea.

In one embodiment, the formaldehyde stabilizer package contains a guanamine compound. The guanamine compound may include an aliphatic guanamine-based compound, an alicyclic guanamine-based compound, an aromatic guanamine-based compound, a hetero atom-containing guanamine-based compound, or the like. In one embodiment, the guanamine compound comprises a benzoguanamine. When included in the composition, the guanamine compound can be present in the polymer composition in an amount of at least about 0.05% by weight, such as in an amount of at least about 0.1% by weight, such as in an amount of at least about 0.3% by weight, such as in an amount of at least about 0.5% by weight. The guanamine compound is generally present in the composition in an amount less than about 2% by weight, such as in an amount less than about 1.5% by weight, such as in an amount less than about 1% by weight, such as less than about 0.8% by weight.

The formaldehyde stabilizer package may also include hydantoin or a substituted hydantoin. One example of a substituted hydantoin is allantoin. Allantoin is also known as (2,5-dioxo-4-imidazolidinyl) urea and has the chemical formula $C_4H_6N_4O_3$. Allantoin has been found to reduce formaldehyde emissions even when one or more light stabilizers are present in the composition. When included in the composition, hydantoin or a substituted hydantoin may be present generally in an amount less than about 1.5% by weight, such as in an amount less than about 1% by weight, such as in an amount less than about 0.5% by weight, such as in an amount less than about 0.3% by weight, such as in an amount less than about 0.2% by weight. The hydantoin or substituted hydantoin can generally be present in an amount greater than about 0.001% by weight.

The formaldehyde stabilizer package may also contain an amino acid in conjunction with at least one of the other emission control agents. The amino acid, for instance, may comprise an α-amino acid, a β-amino acid, a γ-amino acid, a δ-amino acid, and mixtures thereof. For instance, the amino acid may comprise a monoaminomonocarboxylic acid or a monoaminodicarboxylic acid. Examples include glycine, alanine, valine, norvaline, leucine, norleucine, isoleucine, phenylalanine, tyrosine, diiodotyrosine, surinamine, threonine, serine, proline, hydroxyproline, tryptophan, methionine, cystine, cysteine, citrulline, α-aminobutyric acid, hexahydropicolinic acid, teanine, aspartic acid, glutamic acid, asparagine, glutamine, hexahydrodipicolinic acid, hexahydroquinolinic acid, and mixtures thereof. Other amino acids that may be used include diaminomonocarboxylic acids such as lysine, hydroxylysine, arginine, histidine, or mixtures thereof. One amino acid particularly well suited for use in the present disclosure, for instance, is arginine. Arginine can be considered an aliphatic amino acid.

When present in the composition, an amino acid can be included in an amount generally less than about 2% by weight, such as in an amount less than about 1.5% by weight, such as in an amount less than about 1% by weight, such as in an amount less than about 0.5% by weight, such as in an amount less than about 0.3% by weight, such as in an amount less than about 0.2% by weight. The amino acid is generally present in an amount greater than about 0.001% by weight.

The formaldehyde stabilizer package of the present disclosure can be made up of various different combinations of the emission control agents depending upon the particular application and the desired result. In one embodiment, for instance, the formaldehyde stabilizer package includes a guanamine compound in combination with at least one of the other emission control agents. For instance, the guanamine compound can be combined with allantoin and/or arginine. In one embodiment, the formaldehyde stabilizer package includes a combination of the guanamine compound, hydantoin, a substituted hydantoin, and an amino acid.

In an alternative embodiment, the formaldehyde stabilizer package does not contain a guanamine compound such as benzoguanamine. For instance, the formaldehyde stabilizer package can be guanamine-free. In one embodiment, for instance, the formaldehyde stabilizer package comprises a combination of a substituted hydantoin, such as allantoin, and an amino acid, such as arginine. In still another embodiment, the formaldehyde stabilizer package may comprise a blend of hydantoin, a substituted hydantoin, an amino acid, and an ethylene urea.

In one embodiment, the formaldehyde stabilizer package may also contain an ethylene urea, such as 2-imidazolidone or 2-imidazolidinone. For example, one embodiment may contain a compound of the following formula:

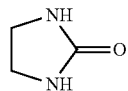

The ethylene urea may be found in some embodiments in an amount greater than about 0.001% by weight, such as greater than about 0.01% by weight, such as greater than about 0.1% by weight, such as greater than about 1% by weight, such as greater than about 3% by weight. In some embodiments, the ethylene urea may be present in amounts less than about 5% by weight, such as less than about 3% by weight, such as less than about 1% by weight, such as less than about 0.1% by weight.

Advantageously, the ethylene urea may, in some embodiments, be combined with at least one other formaldehyde stabilizing compound for synergistic effect. For instance, the ethylene urea may be combined with benzoguanimine and/or allantoin.

In each of the formaldehyde stabilizer packages described above, the stabilizer package can include a single amino acid and/or a single substituted hydantoin or at least two amino acids and/or at least two substituted hydantoins.

In addition to a polyoxymethylene polymer and a formaldehyde stabilizer package, the polymer composition of the present disclosure can contain various other additives and ingredients. For instance, in one embodiment, the polymer composition may contain an acid scavenger. The acid scavenger can comprise a carboxylic acid salt.

For instance, the carboxylic acid salt may comprise a salt of a fatty acid, such as a metal salt of a fatty acid. For example, the carboxylic acid salt may comprise an alkaline earth metal salt of a fatty acid. The cation of the salt, for instance, may comprise calcium, barium, lithium, sodium, magnesium, zinc, or the like.

The fatty acid can contain a carbon chain of generally from about 3 carbon atoms to about 20 carbon atoms. The fatty acid may comprise a dicarboxylic acid or a tricarboxylic acid.

In one embodiment, the metal salt of the fatty acid may comprise a metal salt of citric acid, propionic acid, stearic acid, butanoic acid, hexanoic acid, decanoic acid, lauric acid, myristic acid, palmitic acid, and the like. In one particular embodiment, the metal salt of the fatty acid may comprise calcium propionate, calcium 12-hydroxystearate, a calcium citrate such as tricalcium citrate, and mixtures thereof. In one embodiment, when the polyoxymethylene polymer composition includes one or more coloring agents, various benefits and advantages are obtained by combining the coloring agents with calcium propionate.

One or more carboxylic acid salts are generally present in the polymer composition in an amount greater than about 0.05% by weight, such as in an amount greater than about 0.1% by weight, such as in an amount greater than about 0.2% by weight, such as in an amount greater than about 0.3% by weight, such as in an amount greater than about 0.4% by weight, such as in an amount greater than about 0.5% by weight. One or more carboxylic acid salts are generally present in the polymer composition in an amount less than about 5% by weight, such as in an amount less than about 3% by weight, such as in an amount less than about 2% by weight, such as in an amount less than about 1.5% by weight, such as in an amount less than about 1% by weight.

The polymer composition of the present disclosure may also contain other known additives such as, for example, antioxidants, UV stabilizers or heat stabilizers, impact modifiers and/or reinforcing fibers. In addition, the compositions can contain processing auxiliaries, for example adhesion promoters, lubricants, nucleants, demolding agents, fillers, or antistatic agents and additives which impart a desired property to the compositions and articles or parts produced therefrom.

In one embodiment, an ultraviolet light stabilizer may be present. The ultraviolet light stabilizer may comprise a benzophenone, a benzotriazole, or a benzoate. The UV light absorber, when present, may be present in the polymer composition in an amount of at least about 0.01 wt. %, such as at least about 0.05 wt. %, such as at least about 0.075 wt. % and less than about 1 wt. %, such as less than about 0.75 wt. %, such as less than about 0.5 wt. %, wherein the weight is based on the total weight of the respective polymer composition.

In one embodiment, a nucleant may be present. The nucleant may increase crystallinity and may comprise an oxymethylene terpolymer. In one particular embodiment, for instance, the nucleant may comprise a terpolymer of butanediol diglycidyl ether, ethylene oxide, and trioxane. The nucleant may be present in the composition in an amount of at least about 0.01 wt. %, such as at least about 0.05 wt. %, such as at least about 0.1 wt. % and less than about 2 wt. %, such as less than about 1.5 wt. %, such as less than about 1 wt. %, wherein the weight is based on the total weight of the respective polymer composition.

In one embodiment, an antioxidant, such as a sterically hindered phenol, may be present. Examples which are available commercially, are pentaerythrityl tetrakis[3-(3,5-di-tert-butyl-4-hydroxyphenyl)propionate], triethylene glycol bis[3-(3-tert-butyl-4-hydroxy-5-methylphenyl)propionate], 3,3'-bis[3-(3,5-di-tert-butyl-4-hydroxyphenyl) propionohydrazide], and hexamethylene glycol bis[3-(3,5-di-tert-butyl-4-hydroxyphenyl)propionate]. The antioxidant may be present in the polymer composition in an amount of at least about 0.01 wt. %, such as at least about 0.05 wt. %, such as at least about 0.075 wt. % and less than about 1 wt. %, such as less than about 0.75 wt. %, such as less than about 0.5 wt. %, wherein the weight is based on the total weight of the respective polymer composition.

In one embodiment, lights stabilizers, such as sterically hindered amines, may be present in addition to the ultraviolet light stabilizer. Hindered amine light stabilizers that may be used include oligomeric hindered amine compounds that are N-methylated. For instance, hindered amine light stabilizer may comprise a high molecular weight hindered amine stabilizer. Other embodiments of light stabilizers include 2,2,6,6-tetramethyl-4-piperidyl compounds, e.g., bis(2,2,6, 6-tetramethyl-4-piperidyl) sebacate or the polymer of dimethyl succinate and 1-(2-hydroxyethyl)-4-hydroxy-2,2,6,6-tetramethyl-4-piperidine. In one embodiment, the light stabilizer may comprise 2-(2H-benzzotriazol-2-yl) 4,6-bis (1-ethyl-1-phenyl-ethyl)phenol. The light stabilizers, when present, may be present in the polymer composition in an amount of at least about 0.01 wt. %, such as at least about 0.05 wt. %, such as at least about 0.075 wt. % and less than about 1 wt. %, such as less than about 0.75 wt. %, such as less than about 0.5 wt. %, wherein the weight is based on the total weight of the respective polymer composition.

In one embodiment, lubricants may be present. The lubricant may comprise a polymer wax composition. Further, in one embodiment, a polyethylene glycol polymer (processing aid) may be present in the composition. The polyethylene glycol, for instance, may have a molecular weight of from about 1000 to about 5000, such as from about 3000 to about 4000. In one embodiment, for instance, PEG-75 may be present. In another embodiment, a fatty acid amide such as ethylene bis(stearamide) may be present. Lubricants may generally be present in the polymer composition in an amount of at least about 0.01 wt. %, such as at least about 0.05 wt. %, such as at least about 0.075 wt. % and less than about 1 wt. %, such as less than about 0.75 wt. %, such as less than about 0.5 wt. %, wherein the weight is based on the total weight of the respective polymer composition.

In one embodiment, a coloring agent may be present. Coloring agents that may be used include any desired inorganic pigments, such as titanium dioxide, ultramarine blue, cobalt blue, and other organic pigments and dyes, such as phthalocyanines, anthraquinnones, and the like. Other coloring agents include carbon black or various other polymer-soluble dyes. In one embodiment, a combination of coloring agents may be included in the polymer composition. For instance, the polymer composition may contain titanium dioxide in combination with carbon black. In an alternative embodiment, the coloring agents present in the polymer composition may comprise titanium dioxide in combination with at least one color pigment, such as a yellow pigment and a green pigment and optionally further in combination with carbon black. The coloring agent may be present in the composition in an amount of at least about 0.01 wt. %, such as at least about 0.05 wt. %, such as at least about 0.1 wt. %, such as at least about 0.5 wt. %, such as at least about 0.8 wt. %, such as at least about 1 wt. % and less than about 5 wt. %, such as less than about 2.5 wt. %, such as less than about 1 wt. %, wherein the weight is based on the total weight of the respective polymer composition.

Fillers that may be included in the composition include glass beads, wollastonite, loam, molybdenum disulfide or graphite, and/or inorganic or organic fibers.

Reinforcing fibers which may be included in the composition are mineral fibers, such as glass fibers, polymer fibers, in particular organic high-modulus fibers, such as aramid fibers, metal fibers, such as steel fibers, carbon fibers, natural fibers, and/or fibers from renewable resources.

These fibers may be in modified or unmodified form, e.g. provided with a sizing, or chemically treated, in order to improve adhesion to the polymer. Glass fibers are particularly preferred.

Glass fibers are provided with a sizing to protect the glass fiber, to smooth the fiber but also to improve the adhesion between the fiber and the matrix material. A sizing usually comprises silanes, film forming agents, lubricants, wetting agents, adhesive agents optionally antistatic agents and plasticizers, emulsifiers and optionally further additives.

Specific examples of silanes are aminosilanes, e.g. 3-trimethoxysilylpropylamine, N-(2-aminoethyl)-3-aminopropyltrimethoxy-silane, N-(3-trimethoxysilanylpropyl)ethane-1,2-diamine, 3-(2-aminoethyl-amino)propyltrimethoxysilane, N-[3-(trimethoxysilyl)propyl]-1,2-ethane-diamine.

Film forming agents are for example polyvinylacetates, polyesters and polyurethanes. Sizings based on polyurethanes may be used advantageously.

The reinforcing fibers may be compounded into the polyoxymethylene matrix, for example in an extruder or kneader. However, the reinforcing fibers may also advantageously take the form of continuous-filament fibers sheathed or impregnated with the polyoxymethylene molding composition in a process suitable for this purpose, and then processed or wound up in the form of a continuous strand, or cut to a desired pellet length so that the fiber lengths and pellet lengths are identical. An example of a process particularly suitable for this purpose is the pultrusion process.

The reinforcing fibers can be present in the molding composition in an amount ranging from 5 to 45 wt.-%, such as from 10 to 40 wt.-%, wherein the weight is based on the total weight of the composition.

The polymer composition may further comprise an impact modifier such as a thermoplastic elastomer. Thermoplastic elastomers are materials with both thermoplastic and elastomeric properties. Thermoplastic elastomers include styrenic block copolymers, polyolefin blends referred to as thermoplastic olefin elastomers, elastomeric alloys, thermoplastic polyurethanes, thermoplastic copolyesters, and thermoplastic polyamides.

Thermoplastic elastomers well suited for use in the present disclosure are polyester elastomers (TPE-E), thermoplastic polyamide elastomers (TPE-A) and in particular thermoplastic polyurethane elastomers (TPE-U).

In one particular embodiment, a thermoplastic polyurethane elastomer is used. The thermoplastic polyurethane elastomer, for instance, may have a soft segment of a long-chain diol and a hard segment derived from a diisocyanate and a chain extender. In one embodiment, the polyurethane elastomer is a polyester type prepared by reacting a long-chain diol with a diisocyanate to produce a polyurethane prepolymer having isocyanate end groups, followed by chain extension of the prepolymer with a diol chain extender. Representative long-chain diols are polyester diols such as poly(butylene adipate)diol, poly(ethylene adipate)diol and poly(ε-caprolactone)diol; and polyether diols such as poly(tetramethylene ether)glycol, poly(propylene oxide)glycol, poly(ethylene oxide)glycol, polycarbonate diol and/or a polyester polycarbonate diol. Suitable diisocyanates include 4,4'-methylenebis(phenyl isocyanate), 2,4-toluene diisocyanate, 1,6-hexamethylene diisocyanate and 4,4'-methylenebis-(cycloxylisocyanate). Suitable chain extenders are $C_2$-$C_6$ aliphatic diols such as ethylene glycol, 1,4-butanediol, 1,6-hexanediol and neopentyl glycol. One example of a thermoplastic polyurethane is characterized as essentially poly(adipic acid-co-butylene glycol-co-diphenylmethane diisocyanate).

The amount of thermoplastic elastomer contained in the polymer composition can vary depending upon various factors. For instance, the thermoplastic elastomer can be present in an amount ranging from about 0.5% by weight to about 50% by weight. In one embodiment, for instance, a thermoplastic elastomer or impact modifier may be present in the composition in an amount less than about 25% by weight, such as in an amount less than about 15% by weight, such as in an amount less than about 10% by weight. The thermoplastic elastomer or impact modifier is generally present in an amount greater than about 2% by weight, such as in an amount greater than about 5% by weight, such as in an amount greater than about 8% by weight, such as in an amount greater than about 10% by weight.

In one embodiment, when an impact modifier or thermoplastic elastomer is present in the composition, the composition can also include a coupling agent. The coupling agent may comprise a polyisocyanate, such as a diisocyanate or triisocyanate. The coupling agent can be present generally in an amount from about 0.1% to about 2% by weight, such as from about 0.1% to about 1% by weight.

The compositions of the present disclosure can be compounded and formed into a polymer article using any technique known in the art. For instance, the respective composition can be intensively mixed to form a substantially homogeneous blend. The blend can be melt kneaded at an elevated temperature, such as a temperature that is higher than the melting point of the polymer utilized in the polymer composition but lower than the degradation temperature. Alternatively, the respective composition can be melted and mixed together in a conventional single or twin screw extruder. Preferably, the melt mixing is carried out at a temperature ranging from 100 to 280° C., such as from 120 to 260° C., such as from 140 to 240° C. or 180 to 220° C.

After extrusion, the compositions may be formed into pellets. The pellets can be molded into polymer articles by techniques known in the art such as injection molding, thermoforming, blow molding, rotational molding and the like.

The polymer composition of the present disclosure can be used to produce various molded parts. The parts can be formed through any suitable molding process, such as an injection molding process or through a blow molding process. Polymer articles that may be made in accordance with the present disclosure include knobs, door handles, automotive decorative trim pieces, and the like without limitation. Other polymer articles, for instance, that may be made in accordance with the present disclosure include latches, levers, gears, pivot housings, speaker grills, and the like.

For instance, referring to FIG. 1, an automotive interior is shown illustrating various automotive parts that may be made in accordance with the present disclosure. The polymer composition, for instance, may be used to produce automotive part 10, which comprises at least a portion of an interior door handle. The polymer composition may also be used to produce a part on the steering column such as automotive part 12. In general, the polymer composition can be used to mold any suitable decorative trim piece or bezel, such as trim piece 14.

Figure 2:
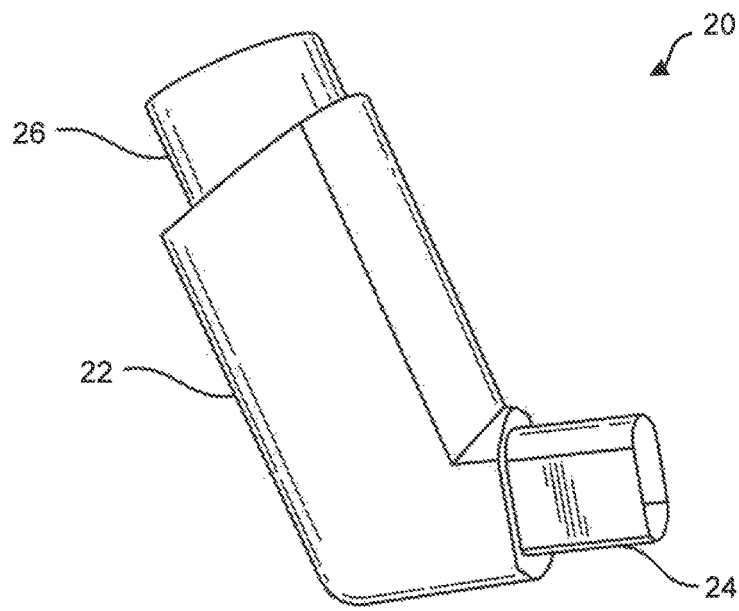
FIG. 2 is a perspective view of a medical inhaler that may be made from molded parts in accordance with the present disclosure.

As described above, in one embodiment, the formaldehyde stabilizer package does not include a guanamine compound. Instead, the formaldehyde stabilizer package can include a combination of a hydantoin, a substituted hydantoin, an amino acid, and/or an ethylene urea. Guanamine-free compositions are particularly well suited for use in producing medical products. For instance, referring to FIG. 2, an inhaler 20 is shown. The inhaler 20 includes a housing 22 attached to a mouthpiece 24. In operative association with the housing 22 is a plunger 26 for receiving a canister containing a composition to be inhaled. The composition may comprise a spray or a powder.

During use, the inhaler 20 administers metered doses of a medication, such as an asthma medication to a patient. The asthma medication may be suspended or dissolved in a propellant or may be contained in a powder. When a patient actuates the inhaler to breathe in the medication, a valve opens allowing the medication to exit the mouthpiece. In accordance with the present disclosure, the housing 22, the mouthpiece 24 and the plunger 26 can all be made from a polymer composition as described above.

Figure 3:
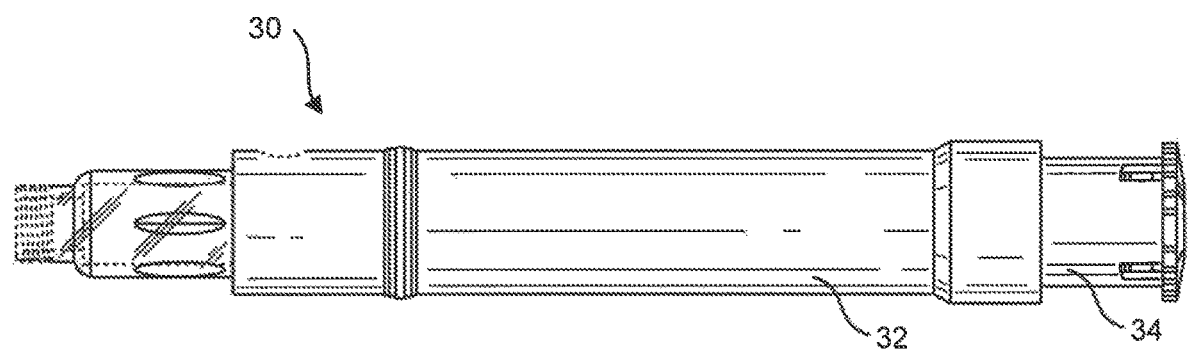
FIG. 3 is a perspective view of a medical injector containing molded parts made in accordance with the present disclosure.

Referring to FIG. 3, another medical product that may be made in accordance with the present disclosure is shown. In FIG. 3, a medical injector 30 is illustrated. The medical injector 30 includes a housing 32 in operative association with a plunger 34. The housing 32 may slide relative to the plunger 34. The medical injector 30 may be spring loaded.

The medical injector is for injecting a drug into a patient typically into the thigh or the buttocks. The medical injector can be needleless or may contain a needle. When containing a needle, the needle tip is typically shielded within the housing prior to injection. Needleless injectors, on the other hand, can contain a cylinder of pressurized gas that propels a medication through the skin without the use of a needle. In accordance with the present disclosure, the housing 32 and/or the plunger 34 can be made from a polymer composition as described above.

While the polyoxymethylene polymer composition and polymer articles produced therefrom of the present disclosure provide improved emission properties, the compositions and articles may also exhibit excellent mechanical properties (ISO Test 527). For example, when tested according to ISO Test No. 527, the polymer composition may have a tensile modulus of greater than about 1,200 MPa, such as greater than about 2,000 MPa. The tensile modulus is generally less than about 10,000 MPa.

The polymer composition can exhibit a notched Charpy impact strength at 23° C. (ISO Test 179-1) of greater than about 3 kJ/m$^2$, such as greater than about 6 kJ/m$^2$. The notched Charpy impact strength is generally less than about 20 kJ/m$^2$.

The present disclosure may be better understood with reference to the following example.

EXAMPLES

The following examples were conducted in order to demonstrate some of the advantages and benefits of polymer compositions made according to the present disclosure.

Example 1

Various polymer compositions were formulated, molded into test specimens, and tested for formaldehyde emission. The polymer compositions contained an oxymethylene copolymer. The polyoxymethylene polymer had a melt volume rate of about 9 cm$^3$/10 min according to ISO Test 1133. In addition to the polyoxymethylene polymer, the polymer composition contained 0.25% by weight of a nucleant, 0.3% by weight of an antioxidant (unless otherwise noted, pentaerythritol tetrakis(3-(3,5-di-tert-butyl-4-hydroxyphenyl)propionate)), 0.18% by weight of a lubricant, and 0.07% by weight of calcium 12 hydroxystearate. In addition, the polymer compositions all contained 1% by weight of a black color concentrate.

Various different additives were then combined with the above polymer composition and tested for formaldehyde emission. Each formulation was compounded on a 32 mm co-rotating twin-screw extruder (ZSK 32, Coperion, Germany). The test plaques were injection molded.

In the initial set of tests, formaldehyde emission was tested similar to a 2011 China Government Test having Test No. GB/T27630-2011. However, instead of using a Tedlar bag sampling method to capture and assess formaldehyde emission, a fixed volume chamber was used. As used herein, this test will be referred to as the "Modified GB/T27630-2011 Test" and the procedure is as follows:

Modified GB/T27630-2011 Test

Sample Considerations:
 Samples are POM plaques (54×79 mm) molded according to VDA275 specifications. Two plaques are used for each measurement. Plaques are conditioned for a 24±2 hours at 23° C. and 50% RH prior to analysis. Samples are analyzed within 15 days of molding.

Figure 4:
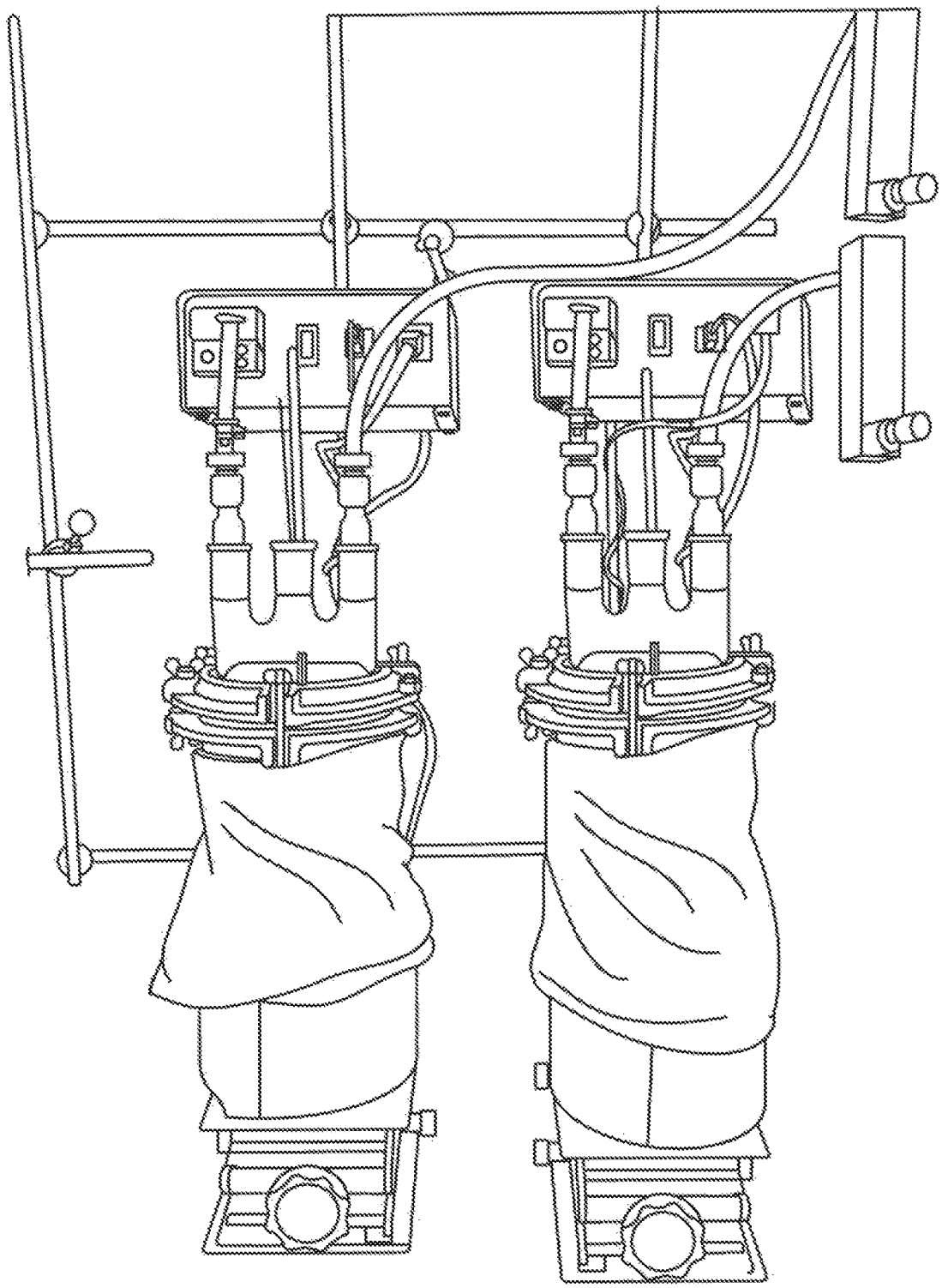
FIG. 4 illustrates the apparatus used to measure formaldehyde emission as described in the example below.

Formaldehyde Collection Setup:
 The collection apparatus is shown in FIG. 4. A 2 liter collection vessel is heated to between 145-160° C. via a heating mantle. Two POM plaques are suspended by a wire hook and separated via a Teflon spacer. The temperature at the center of the plaques is 65° C. with 10° C. variation across the length of the vertical dimension. During testing the vessel is purged with nitrogen at a rate of 500 mL/min. The gas enters the top of the vessel and exits through a DNPH-derivatized cartridge at the distal end of the gas flow path. Formaldehyde emissions are collected for a period of 2 hours, followed by removal of the plaques and a 30 minute purge prior to the next test. The formaldehyde-DNPH cartridge is then washed with 5 mL of acetonitrile and analyzed via HPLC using the parameters listed below. Quantitation was performed using a commercially available mixture of 13 DNPH-derivatized aldehydes and ketones (Cerilliant) including formaldehyde-DNPH. Standards from 0.03 to 15 µg/mL were fit with linear regressions ($R^2$>0.9999).

LC Experimental Conditions:
 System: Dionex Ultimate 3000; LC4
 Column: Phenomenex Kinetex C18 2.1×100 mm, 2.6 µm SN #: H15-038929
 Column Temperature 40° C.
 Injection Volume 2 µL
 Flow Rate 0.400 m L/m in
 Detector Wavelength 365 nm
 Detector bandwidth 10 nm

| HPLC Mobile Phase Gradient | | |
|---|---|---|
| Time (min) | ACN + 0.07% TFA (%) | Water + 0.07% TFA (%) |
| 0 | 30 | 70 |
| 11 | 42 | 58 |
| 12 | 70 | 30 |
| 13.5 | 70 | 30 |
| 13.6 | 30 | 70 |
| 18.8 | 30 | 70 |

Blanks and Controls:
 An unused DNPH capture cartridge was analyzed directly via HPLC without any exposure to the exposure vessels. This blank test resulted in no peak, confirming a zero background with just the DNPH cartridge. A control run was also performed by running the method as normal but without any sample plaques and following a vessel purge. The resultant peak was 0.12% the area of that observed for a typical plaque. This indicates the 30 minute purge is effective at removing emissions from the reactor vessel.

Three commercial formulations were also tested. The first two commercial formulations (Control 1 and Control 2) contained 0.5% by weight benzoguanamine. The chemical composition of the third commercial sample was unknown. The following compositions were tested and the following results were obtained:

TABLE 1

| | Formaldehyde scavengers | Formaldehyde emission (µg/g) |
|---|---|---|
| Control 1 | Benzoguanamine 0.5% | 2.57 |
| Control 2 | Benzoguanamine 0.5% | 2.46 |

TABLE 1-continued

|  | Formaldehyde scavengers | Formaldehyde emission (µg/g) |
|---|---|---|
| Control 3 |  | 0.21 |
| Sample 1 | Melamine 0.07% | 3.93 |
| Sample 2 | dicyandiamide 0.03% | 11.86 |
| Sample 3 | sebacic dihydrazide 0.05% | 10.91 |
| Sample 4 | Allantoin 0.05% | 5.97 |
| Sample 5 | copolyamide 0.15% | 10.89 |
| Sample 6 | Hydantoin 0.1% | 4.90 |
| Sample 7 | Arginine 0.03% | 8.99 |
| Sample 8 | Benzoguanamine 0.5%, Melamine 0.07% | 2.13 |
| Sample 9 | Benzoguanamine 0.5%, dicyandiamide 0.03% | 2.26 |
| Sample 10 | Benzoguanamine 0.5%, sebacic dihydrazide 0.05% | 1.74 |
| Sample 11 | Benzoguanamine 0.5%, Allantoin 0.05% | 0.67 |
| Sample 12 | Benzoguanamine 0.5%, copolyamide 0.15% | 2.13 |
| Sample 13 | Benzoguanamine 0.5%, Hydantoin 0.1% | 1.25 |
| Sample 14 | Benzoguanamine 0.5%, Arginine 0.03% | 1.04 |

As shown above, Sample Nos. 11, 13 and 14 demonstrated dramatic reductions in formaldehyde emissions, especially in comparison to compositions only containing a guanamine compound.

Further polyoxymethylene polymer compositions were then formulated and tested using the same formaldehyde emission test with benzoguanamine (BZG), arginine (ARG), and allantoin (ALT). The following results were obtained:

TABLE 2

|  | Scavengers | Formaldehyde emission (µg/g) |
|---|---|---|
| Control 1 | BZG 0.5% | 2.57 |
| Sample 15 | BZG 0.6% | 1.84 |
| Sample 16 | BZG 0.5%, ALT 0.1% | 0.19 |
| Sample 17 | ALT 0.1% | 1.42 |
| Sample 18 | BZG 0.5%, ARG 0.1% | 0.28 |
| Sample 19 | ARG 0.1% | 1.11 |

Further polyoxymethylene polymer compositions were then formulated containing the combination of benzoguanamine and allantoin. In addition, two different acid scavengers were tested. Specifically, calcium propionate was tested in addition to calcium 12 hydroxystearate.

The compositions were then tested for formaldehyde emission using different tests and tested for total volatile organic compounds. The physical properties of the formulations were also tested. The first test for formaldehyde emissions was as described above. The second test for formaldehyde emissions was conducted according to VDA Test 275. The test for total volatile organic compounds (TVOC) was conducted similar to the first formaldehyde emission test using a fixed volume chamber. The outgas from the chamber, however, was sent to a Tenac cartridge and analyzed by GC-MS.

Tensile module, tensile stress at yield, and tensile strain at yield were all tested according to ISO Test 527 at 23° C. Notched Charpy impact strength was measured at 23° C. according to ISO Test 179-1.

For purposes of comparison, two controls were also tested. Control 1 was the same as in Table 1 above and contained 0.5% benzoguanamine. Control 4, on the other hand, was a commercial product whose composition is unknown. The following results were obtained:

TABLE 3

|  | Composition 1 | Modified GB Test (µg/g) | VDA 275 (µg/g) | TVOC (µg/g) | Tensile Modulus (MPa) | Tensile Stress at yield (MPa) | Tensile Strain at yield (%) | Notched Charpy (kJ/m²) |
|---|---|---|---|---|---|---|---|---|
| Control 1 | BZG 0.5% | 2.15 | 0.80 | 0.53 | 2584 | 64 | 10 | 7.0 |
| Control 4 |  | 1.14 | 1.47 | 0.33 | 2525 | 61 | 10 | 6.2 |
| Sample 16 | BZG 0.5%, ALT 0.1%, Ca 12 Hydroxy Stearate 0.07% | 0.1 | 0.59 | 0.29 | 2529 | 64 | 10 | 7.1 |
| Sample 20 | BZG 0.5%, ALT 0.1%, Ca propionate 0.07% | 0.16 | 0.74 | 0.33 | 2564 | 64 | 10 | 6.4 |
| Sample 18 | BZG 0.5%, ARG 0.1%, Ca 12 Hydroxy Stearate 0.07% | 0.2 | 0.27 | 0.34 | 2600 | 64 | 10 | 6.4 |
| Sample 21 | BZG 0.5%, ARG 0.1%, Ca propionate 0.07% | 0.27 | 0.38 | 0.29 | 2598 | 64 | 10 | 6.4 |

During the test, it was noticed that the calcium propionate acid scavenger was more compatible with the coloring agent, a 1% black color concentrate, than the calcium 12 hydroxystearate.

Example 2

Further tests were conducted with formulations made in accordance with the present disclosure. The tests were the same as described in Example 1 above. In this example, the polyoxymethylene polymer had a higher melt flow rate. Specifically, the polyoxymethylene polymer had a melt flow rate of 27 cm³/10 min. The compositions are otherwise the same as in Example 1, except a UV stabilizer was used at 0.4%, a lubricant was used at 0.5%, and calcium propionate was substituted for calcium 12 hydroxystearate. Control 5, however, used 0.05% tricalcium citrate instead of the calcium propionate and 0.2% lubricant instead of 0.18% lubricant.

In this test, different color agent packages were incorporated into the polymer compositions and different hindered amine light stabilizers were used (HAL) at 0.5%. The formulations were compared to Control 5 which contained the same polyoxymethylene polymer in combination with 0.5% by weight benzoguanamine. Control 5 and Sample 22 were produced on a twin-screw and Samples 23 through 28 were produced on a single-screw compounder. The following results were obtained:

TABLE 4

| | Formaldehyde Scavengers and Color Package | Modified GB Test (μg/g) | VDA275 (μg/g) | TVOC (μg/g) |
|---|---|---|---|---|
| Control 5 | BZG 0.5%, 1% Black | 2.58 | 1.08 | 0.20 |
| Sample 22 | BZG 0.5%, ALT 0.1% Black | 0.59 | 0.86 | 0.20 |
| Sample 23 | BZG 0.5%, ALT 0.1% Natural | 0.14 | 0.57 | 0.76 |
| Sample 24 | BZG 0.5%, ALT 0.1%, Tan | 0.18 | 0.60 | 0.87 |
| Sample 25 | BZG 0.5%, ARG 0.1%, GRAY | 0.17 | 0.59 | 0.43 |
| Sample 26 | BZG 0.5%, ARG 0.1%, GRAY, Alternate HAL-1 | 0.15 | 0.57 | 0.44 |
| Sample 27 | BZG 0.5%, ARG 0.1%, GRAY, Alternate HAL-2 | 0.17 | 0.67 | 0.47 |
| Sample 28 | BZG 0.5%, ARG 0.1%, Black | 0.16 | 0.65 | 0.31 |

Example 3

Further compositions were tested using the same base resin and additives as in Example 1. Table 5 shows additional results of the synergistic effect of arginine (ARG) and benzoguanamine (BZG) on the emission performance of POM. Control 6 is composed of 0.5% benzoguanamine. Samples 29, 30, and 31 are composed of arginine alone, a combination of arginine and benzoguanamine, and benzoguanamine alone, respectively, at the same loading level, i.e. 0.6%. Combination of 0.1% arginine and 0.5% benzoguanamine shows significantly lower formaldehyde (FA) emissions by both the Modified GB and VDA275 methods, as well as the TVOC emission, than the arginine alone or benzoguanamine alone samples. This indicates that there is a synergistic effect between arginine and benzoguanamine in formaldehyde scavenging. Compared to the control, the 0.1% arginine and 0.5% benzoguanamine combination demonstrated approximately 5.8 times improvement in formaldehyde emission by the modified GB Test, 2 times improvement by VDA275 methods, and approximately 11 times improvement in TVOC emission.

TABLE 5

| | Composition | Modified GB Test (μg/g) | VDA275 (μg/g) | TVOC (μg/g) |
|---|---|---|---|---|
| Control 6 | ARG 0%, BZG 0.5% | 1.73 | 0.72 | 2.30 |
| Sample 29 | ARG 0.6%, BZG 0% | 1.16 | 0.48 | 1.10 |
| Sample 30 | ARG 0.1%, BZG 0.5% | 0.30 | 0.36 | 0.21 |
| Sample 31 | ARG 0%. BZG 0.6% | 0.90 | 0.49 | 0.17 |

Example 4

Further compositions were tested using the same base resin and additives as in Example 1. Table 6 shows an example combination of allantoin (ALT) and arginine and its emission performance. Control 7 is a POM sample without an formaldehyde scavenger such as benzoguanamine, allantoin, or arginine. Sample 32 includes the combination of 0.1% allantoin and 0.1% arginine. By adding the combination of 0.1% allantoin and 0.1% arginine to the POM of Control 7, the formaldehyde emissions were reduced by approximately 145 times via the Modified GB Test and 26 times via VDA275. This is also approximately 25 times better by the Modified GB Test and 1.1 times better by VDA275, in formaldehyde emission, than Control 6.

TABLE 6

| | Composition | Modified GB Test (μg/g) | VDA275 (μg/g) |
|---|---|---|---|
| Control 7 | No formaldehyde scavenger added | 10.19 | 17.31 |
| Control 6 | ARG 0%, BZG 0.5% | 1.73 | 0.72 |
| Sample 32 | ALT 0.1%, ARG 0.1% | 0.07 | 0.66 |

Benzoguanamine may not be suitable for use in some applications; for example, various regulations may restrict the amount of benzoguanamine used in a particular product. In contrast, arginine (L-arginine, CAS #74-79-3) is an amino acid, and allantoin (CAS #97-59-6) is widely used in cosmetics and pharmaceutical applications. Use of less restricted ingredients, such as allantoin and arginine, not only achieves better performance than existing solutions, but also could expand the application of low emission POM, such as to heavily regulated products.

Example 5

Further compositions were tested using the same base resin and additives as in Example 1, except that Samples 34-36 were produced with a substituted POM polymer having a melt volume rate of about 8 cm$^3$/10 min according to ISO Test 1133, and Samples 35 and 36 contain 1% of a black color concentrate. Combinations of allantoin, arginine, and benzoguanamine were also investigated in formaldehyde emission performance. The following mixtures were considered: allantoin at 0%, 0.075%, 0.15%, 0.225% loadings, arginine at 0%, 0.05%, 0.075%, 0.15%, 0.225% loadings, benzoguanamine at 0%, 0.25%, 0.5%, 0.75% loadings, and their combinations. Some examples of the study are shown in Table 7. Among studied samples, the combination of 0.1% allantoin, 0.15% arginine, and 0.5% benzoguanamine (Sample 34 and Sample 36) performed best in formaldehyde and TVOC emissions.

TABLE 7

| | Description | Composition | Modified GB Test (μg/g) | VDA275 (μg/g) | TVOC (μg/g) |
|---|---|---|---|---|---|
| Control 6 | Natural | ALT 0%, ARG 0%, BZG 0.5% | 1.73 | 0.72 | 2.30 |
| Sample 33 | Natural | ALT 0.1%, ARG 0.05%, BZG 0.5% | 0.08 | 0.51 | 0.01 |
| Sample 34 | Natural | ALT 0.1%, ARG 0.15%, BZG 0.5% | 0.02 | 0.05 | 0.01 |
| Sample 35 | Black | ALT 0.1%, ARG 0.05%, BZG 0.5% | 0.06 | 0.14 | 0.02 |
| Sample 36 | Black | ALT 0.1%, ARG 0.15%, BZG 0.5% | 0.01 | 0.11 | 0.01 |

Both natural samples and samples tinted with a 1% mixture of a black color concentrate were tested. The combination in a natural POM sample showed approximately 87 times lower formaldehyde emission by the Modified GB Test, 15 times lower formaldehyde emission by VDA275, and 230 times lower TVOC emission than Control 6. The same combination in a black sample showed 173 times lower formaldehyde emission by the Modified GB Test, 6.3 times lower formaldehyde emission by VDA275, and 230 times lower TVOC emission than the control. The natural sample of 0.1% allantoin, 0.15% arginine, and 0.5% benzoguanamine (Sample 34) showed a noticeable yellowness, compared to a typical unfilled POM. The black sample, Sample 36, can be still used because the yellowness caused by the additives is masked by black pigment.

The combination of 0.1% allantoin, 0.05% arginine, and 0.5% benzoguanamine showed the second-best formaldehyde emission scavenging performance. Such combination in a natural sample (Sample 33) showed approximately 22 times lower formaldehyde emission by the Modified GB Test, approximately 1.4 times lower formaldehyde by VDA275, and 230 times lower TVOC compared to Control 6. The same combination in a black sample (Sample 35) showed approximately 29 times lower formaldehyde emission by the Modified GB Test, approximately 5 times lower formaldehyde by VDA275, and 115 times lower TVOC compared to the control. Although these results are significant improvement from the control, and the combinations discussed previously, these samples demonstrated slightly higher formaldehyde emission than 0.1% allantoin, 0.15% arginine, and 0.5% benzoguanamine while being slightly yellower than a typical unfilled POM.

Example 6

Both the combination of 0.1% allantoin, 0.05% arginine, and 0.5% benzoguanamine and the combination of 0.1% allantoin, 0.15% arginine, and 0.5% benzoguanamine were trialed in a UV stabilized formulation, with 0.5% HAL, a phenolic UV stabilizer, and a polyethylene glycol and POM, in gray, tan, and black colors. The emission level by the Modified GB Test was between 0.05 ppm to 0.1 ppm, which is a 20 to 40 times improvement compared to the control. The formaldehyde emission by VDA275 method was improved by approximately 5 times improved from the control.

Example 7

Further compositions were tested using the same base resin and additives as used in Sample 34 of Example 5, except that the level of antioxidant was increased to 0.4%. In the following example, the combination of 0.1 allantoin, 0.05% arginine, and 0.5% benzoguanamine was further optimized to tone down the yellowness and to improve the emission performance of Sample 33. Some examples are shown in Table 8.

TABLE 8

| | Composition | Color L rating | Color a rating | Color b rating | Modified GB Test (µg/g) | VDA275 (µg/g) | TVOC (µg/g) |
|---|---|---|---|---|---|---|---|
| Sample 37 | ALT 0.1%, ARG 0.05%, BZG 0.5%, AO-1 0.4% | 91.4 | −3.13 | 10.5 | 0.033 | 0.076 | 0.02 |
| Sample 38 | ALT 0.1%, ARG 0.05%, BZG 0.5%, AO-2 0.4%, brightener 0.01% | 94.4 | −5.98 | 6.42 | 0.019 | 0.056 | 0.02 |
| Sample 39 | ALT 0.1%, ARG 0.05%, BZG 0.5%, AO-1 0.4%, brightener 0.01% | 94.8 | −5.68 | 4.56 | 0.021 | 0.066 | 0.02 |
| Sample 56 | ALT 0.1%, ARG 0.05%, BZG 0.5%, AO-2 0.4%, No Ca12 hydroxystearate | 91.90 | −2.66 | 8.11 | 0.015 | 0.037 | — |

In Sample 37, the antioxidant (AO) loading was increased to 0.4% in this study, compared to Sample 33. The formaldehyde emission of Sample 37 reduced by approximately 2.4 times by the Modified GB Test and 6.7 times by VDA275 compared to Sample 33. In Sample 38 and Sample 39, the same antioxidant loading level was also used, and both samples included an optical brightener (OB) at 0.01% loading. Sample 38 used AO-2 (ethylenebis(oxyethylene) bis-(3-(5-tert-butyl-4-hydroxy-m-tolyl)-propionate)) and Sample 39 used AO-1 (pentaerythritol tetrakis(3-(3,5-di-tert-butyl-4-hydroxyphenyl)propionate)) as an antioxidant.

Sample 38 and Sample 39 demonstrated similar emission levels slightly improved from Sample 37. When an optical brightener was used, the yellowness of the 0.1% allantoin, 0.05% arginine, and 0.5% benzoguanamine combination was improved, as indicated by the 'b' rating of LAB color measurement.

However, after 1000 hours of exposure to fluorescent light, the color shift of Sample 38 and Sample 39 was noticeable as the optical brightener loses its effect. Sample 56 was yellower than Sample 38 and Sample 39 to start with, but the color does not shift because there is no optical brightener. The formaldehyde emission performance of Sample 56 was significantly improved. Sample 56 has an acceptable yellowness, although not the best, and great formaldehyde emission performance, and may be used as a general purpose, medium flow, extreme low emission POM.

Example 8

Some scavenger packages, such as those that may use 0.5% benzoguanamine, are not generally used in some grades of POM, such as those in which an impact modifier thermoplastic polyurethane (TPU) is conjugated to POM. It is believed that benzoguanamine may, in some cases, interfere the coupling reaction of TPU and POM. In order to achieve lower formaldehyde emission in such POM grades, a higher antioxidant loading has been used. The possibility of using the combination of allantoin and arginine in such grades was studied by representing said grades by Control 8, as shown in Table 9. Control 9 is the low emission version of Control 8, achieved not by 0.5% benzoguanamine but by 0.5% antioxidant loading. Unless otherwise noted, the compositions include 18% TPU, 0.2% antioxidant, 0.15% lubricant, 0.5% diisocyanate coupling agent, and the balance percentage of POM resin.

When either allantoin or arginine was used alone at 0.1%, the formaldehyde emission was significantly reduced compared to the controls. When the combination of allantoin and arginine was used, the formaldehyde reduction was remarkable. The combination of 0.05% allantoin and 0.05% arginine (Sample 42) demonstrated almost a half of formaldehyde emission level compared to allantoin alone or arginine alone at 0.1% loading, which indicates the synergistic effect of the allantoin and arginine combination. The combination of 0.075% allantoin and 0.075% arginine (Sample 43), showed 80 times reduced formaldehyde emission by the Modified GB Test, and approximately 9.4 times reduced formaldehyde emission by VDA275.

TABLE 9

| | Composition | Modified GB Test (µg/g) | VDA275 (µg/g) | TVOC (µg/g) |
|---|---|---|---|---|
| Control 8 | No FA scavenger | 4.97 | 1.995 | 0.31 |
| Control 9 | No FA scavenger, AO-1 0.5% | 3.19 | 1.231 | 0.41 |
| Sample 40 | ALT 0.1%, ARG 0% | 0.14 | 0.540 | 0.39 |
| Sample 41 | ALT 0%, ARG 0.1% | 0.12 | 0.120 | 0.49 |
| Sample 42 | ALT 0.05%, ARG 0.05% | 0.06 | 0.163 | 0.34 |
| Sample 43 | ALT 0.075%, ARG 0.075% | 0.04 | 0.131 | 1.52 |

Example 9

The efficacy of ethylene urea (EU) as a formaldehyde scavenger was evaluated using a 0.1% loading of ethylene urea in POM compositions using the same base resin and additives as used in Sample 34 of Example 5. Table 10 shows the formaldehyde emission results of adding 0.1% ethylene urea of 3 different hydration and purities to POM. As shown in Table 10, ethylene urea was greatly effective in reducing the formaldehyde emission at 0.1% loading. By the modified GB Test method, the formaldehyde emission of a 99% purity hemihydrate ethylene urea containing sample (Sample 44) was approximately 12 times lower than Control 10. By the VDA275 method, the formaldehyde emission of the same sample was approximately 2.5 times lower than Control 10. When Sample 44 and Sample 46 are compared, the formaldehyde emission appears lower when a hemihydrate was used than an anhydrous; however, they both are effective in formaldehyde scavenging. Without wishing to be bound by any particular theory, hydration may help the nitrogen of ethylene urea become more electrophilic to accept formaldehyde.

TABLE 10

| | Composition | Modified GB Test (µg/g) | VDA275 (µg/g) |
|---|---|---|---|
| Control 10 | No formaldehyde scavenger | 0.948 | 0.917 |
| Sample 44 | 0.1% EU (hemihydrate 99%) | 0.076 | 0.358 |
| Sample 45 | 0.1% EU (hemihydrate 87%) | 0.079 | 0.536 |
| Sample 46 | 0.1% EU (anhydrous 96%) | 0.094 | 0.421 |

Example 10

Further examples were conducted to investigate the efficacy of ethylene urea as a formaldehyde scavenger in the presence of other scavengers in POM compositions using the same base resin and additives as used in Sample 34 of Example 5. The ethylene urea used in this example was in hemihydrate form at 99% purity. Sample 55 substituted the antioxidant for 0.4% AO-2 and omitted the calcium 12 hydroxystearate.

Table 11 shows some example combinations of formaldehyde scavengers and results. It appears that the addition of ethylene urea helps reduce the formaldehyde emission level significantly, for example, as compared to the result of its counterpart itself. When all four formaldehyde scavengers are all used, the best emission performance was achieved (Sample 49). However the yellowness of Sample 49 was significant.

Sample 55 is similar to Sample 56, but 0.05% arginine was replaced with 0.05% ethylene urea. The formaldehyde emission performance of Sample 55 was similar to that of Sample 56 by the Modified GB Test, but almost twice high by VDA275. This may be because arginine is especially effective in scavenging under the VDA275 emission testing conditions. However, it was noted that Sample 55 showed significantly better performance in color: its yellowness was comparable to the sample with no formaldehyde scavengers (Sample 47). It seems that the ethylene urea loading level in Sample 55 can be further optimized to achieve the similar formaldehyde emission level of Sample 38, 39 or 56, without compromising the yellowness.

TABLE 11

| | Composition | Modified GB Test (µg/g) | VDA275 (µg/g) | Color L rating | Color a rating | Color b rating |
|---|---|---|---|---|---|---|
| Sample 47 | ALT 0%, ARG 0%, BZG 0%, EU 0% | 0.948 | 0.174 | 92.4 | −0.39 | 1.53 |
| Sample 48 | ALT 0%, ARG 0%, BZG 0.5%, EU 0.1% | 0.050 | 0.083 | 92.2 | −0.67 | 2.10 |

TABLE 11-continued

| Composition | | Modified GB Test (μg/g) | VDA275 (μg/g) | Color L rating | Color a rating | Color b rating |
|---|---|---|---|---|---|---|
| Sample 49 | ALT 0.1%, ARG 0.1%, BZG 0.5%, EU 0.1% | 0.011 | 0.045 | 91.1 | −3.20 | 12.8 |
| Sample 50 | ALT 0%, ARG 0.1%, BZG 0%, EU 0.1% | 0.049 | 0.038 | 91.3 | −2.08 | 8.86 |
| Sample 51 | ALT 0.1%, ARG 0%, BZG 0%, EU 0.1% | 0.051 | 0.164 | 92.20 | −2.21 | 5.69 |
| Sample 52 | ALT 0.1%, ARG 0%, BZG 0.5%, EU 0% | 0.028 | 0.150 | 91.90 | −2.21 | 5.42 |
| Sample 53 | ALT 0.1%, ARG 0.1%, BZG 0%, EU 0% | 0.014 | 0.057 | 91.60 | −3.19 | 11.2 |
| Sample 54 | ALT 0%, ARG 0.1%, BZG 0.5%, EU 0% | 0.031 | 0.063 | 91.70 | −1.96 | 7.03 |
| Sample 55 | ALT 0.1%, BZG 0.5%, EU 0.05% | 0.017 | 0.080 | 92.40 | −0.74 | 1.24 |

Example 11

Further tests were conducted to characterize the efficacy of ethylene urea in combination with other formaldehyde scavengers.

Samples were prepared as follows. Control 11 and Samples 57-60 contained a polyoxymethylene polymer 1 (POM-1) having a dissolved oxygen content of 5.6%. Control 12 and Samples 61-64 contained a polyoxymethylene polymer 2 (POM-2) having a dissolved oxygen content of 2.8%. POM-2, in particular, has a melt flow rate of 2.2 cm$^3$/10 min measured according to ISO 1133.

Control 12 and Samples 61-64 also contained 4.5% of a polyethylene-based acrylonitrile-styrene copolymer.

Each sample and control included 0.25% of a polyoxymethylene terpolymer as a nucleant, ethylene bis(oxyethylene) bis-(3-(5-tert-butyl-4-hydroxy-m-tolyl)-propionate) as an antioxidant (AO), 0.2% ethylene bis(stearamide), and 0.05% tricalcium citrate.

Additional additives were included in the amounts shown in Table 12.

TABLE 12

| | Composition |
|---|---|
| Control 11 | AO 0.25%, BZG 0.5% |
| Control 12 | AO 0.3%, BZG 0.5% |
| Sample 57 | AO 0.25%, EU 0.1% |
| Sample 58 | AO 0.25%, BZG 0.5%, EU 0.1% |
| Sample 59 | AO 0.25%, EU 0.1%, ALT 0.1% |
| Sample 60 | AO 0.25%, BZG 0.5%, EU 0.1%, ALT 0.1% |
| Sample 61 | AO 0.3%, EU 0.1% |
| Sample 62 | AO 0.3%, BZG 0.5%, EU 0.1% |
| Sample 63 | AO 0.3%, EU 0.1%, ALT 0.1% |
| Sample 64 | AO 0.3%, BZG 0.5%, EU 0.1%, ALT 0.1% |

Results of the tests are provided in Table 13.

TABLE 13

| | VDA-275 (μg/g) | | | Modified GB Test (μg/g) |
|---|---|---|---|---|
| | $T_m = 185°$ C. | $T_m = 205°$ C. | $T_m = 215°$ C. | |
| Control 11 | 1.80 | 3.30 | 4.00 | 3.5 |
| Control 12 | 4.70 | 7.90 | 13.60 | 3.43 |
| Sample 57 | 0.26 | 0.8 | 1.47 | 0.39 |
| Sample 58 | 0.40 | 0.70 | 0.94 | 0.40 |
| Sample 59 | 0.35 | 0.76 | 1.58 | 0.067 |
| Sample 60 | 0.7 | 0.86 | 1.10 | 0.084 |
| Sample 61 | 0.63 | 2.60 | 11.00 | 1.13 |
| Sample 62 | 1.26 | 2 | 4.16 | 3.18 |
| Sample 63 | 0.67 | 1.36 | 5.33 | 0.232 |
| Sample 64 | 0.88 | 1.26 | 4.27 | 0.367 |

The above results demonstrate the synergistic emission reduction of ethylene urea in combination with benzoguanimine and/or allantoin. The effect is especially dramatic at higher temperatures.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A polymer composition comprising:
   a polyoxymethylene polymer; and
   a formaldehyde stabilizer package for reducing formaldehyde emissions, the formaldehyde stabilizer package comprising a blend of emission control agents, the blend including a substituted hydantoin, an amino acid, and a guanamine compound.

2. A polymer composition as defined in claim 1, wherein the substituted hydantoin comprises allantoin.

3. A polymer composition as defined in claim 1, wherein the substituted hydantoin is present in an amount less than about 0.5% by weight and in an amount greater than about 0.001% by weight.

4. A polymer composition as defined in claim 1, wherein the guanamine compound comprises benzoguanamine.

5. A polymer composition as defined in claim 1, wherein the guanamine compound is present in the composition in an amount greater than about 0.4% by weight and being present in an amount less than about 2% by weight.

6. A polymer composition as defined in claim 1, wherein the polymer composition exhibits a formaldehyde emission of less than about 5 ppm when tested according to VDA Test 275.

7. A polymer composition as defined in claim 1, wherein the polymer composition exhibits a formaldehyde emission of less than about 4 ppm when tested according to VDA Test 275.

8. A polymer composition as defined in claim 1, wherein the polymer composition exhibits a formaldehyde emission of less than about 3 ppm when tested according to VDA Test 275.

9. A polymer composition as defined in claim 1, wherein the polymer composition further contains a nucleant in an amount from about 0.05% by weight to about 1% by weight, an antioxidant in an amount from about 0.05% to about 2% by weight, and a lubricant in an amount from about 0.05% to about 1.5% by weight.

10. A polymer composition as defined in claim 1, wherein the guanamine compound is present in the polymer composition in an amount from about 0.3% to about 0.8% by weight.

11. A polymer composition as defined in claim 1, wherein the polymer composition has a tensile modulus of at least 1200 MPa when tested according to ISO Test 527 at 23° C., has a tensile strain at yield of greater than about 7% when tested according to ISO Test 527 at 23° C. and has a notched Charpy impact strength of greater than about 3 kJ/m$^2$ when tested according to ISO Test 179-1 at 23° C.

12. A molded article made from a polymer composition of claim 1.

13. A molded article as defined in claim 12, wherein the molded article comprises a medical product.

14. A molded article as defined in claim 13, wherein the medical product comprises an inhaler or an injector.

15. A polymer composition as defined in claim 1, wherein the amino acid comprises arginine.

* * * * *